(12) United States Patent
Ladva

(10) Patent No.: US 9,055,809 B1
(45) Date of Patent: Jun. 16, 2015

(54) ORAL HYGIENE TOOL

(71) Applicant: Suresh Kurji Ladva, Brea, CA (US)

(72) Inventor: Suresh Kurji Ladva, Brea, CA (US)

(*) Notice: Subject to any disclaimer, the term of this patent is extended or adjusted under 35 U.S.C. 154(b) by 0 days.

(21) Appl. No.: 14/305,549

(22) Filed: Jun. 16, 2014

Related U.S. Application Data

(60) Provisional application No. 61/923,206, filed on Jan. 2, 2014.

(51) Int. Cl.
*A46B 15/00* (2006.01)
*A61B 17/24* (2006.01)

(52) U.S. Cl.
CPC ........... *A46B 15/0081* (2013.01); *A61B 17/244* (2013.01)

(58) Field of Classification Search
CPC .......................... A46B 15/0081; A61B 17/244
USPC ............... 15/111; 606/161; D4/108; D24/147
See application file for complete search history.

(56) References Cited

U.S. PATENT DOCUMENTS

| | | | |
|---|---|---|---|
| 1,495,675 A * | 5/1924 | Colt | 132/309 |
| 1,728,956 A | 9/1929 | Darmitzel | |
| 2,574,654 A * | 11/1951 | Moore | 606/161 |
| 2,651,068 A | 9/1953 | Seko | |
| 4,455,704 A * | 6/1984 | Williams | 15/111 |
| 5,980,541 A | 11/1999 | Tenzer | |
| D508,325 S | 8/2005 | Zunga | |
| D515,817 S | 2/2006 | Siemer | |
| 2009/0235474 A1 * | 9/2009 | Seigel | 15/111 |

* cited by examiner

*Primary Examiner* — Mark Spisich
(74) *Attorney, Agent, or Firm* — Karich & Associates; Eric Karich

(57) ABSTRACT

An oral hygiene tool has a tongue scraper with an elongate scraper body having an elongate upper edge forming a scraping surface for the tongue, and an elongate connector body connected to the elongate scraper body. There oral hygiene tool also has a toothbrush with an elongate toothbrush body and a plurality of brushes. The elongate connector body of the tongue scraper is telescopingly engaged with the elongate toothbrush body of the toothbrush, so that the tongue scraper can move between a collapsed configuration and an extended configuration relative to the toothbrush.

6 Claims, 4 Drawing Sheets

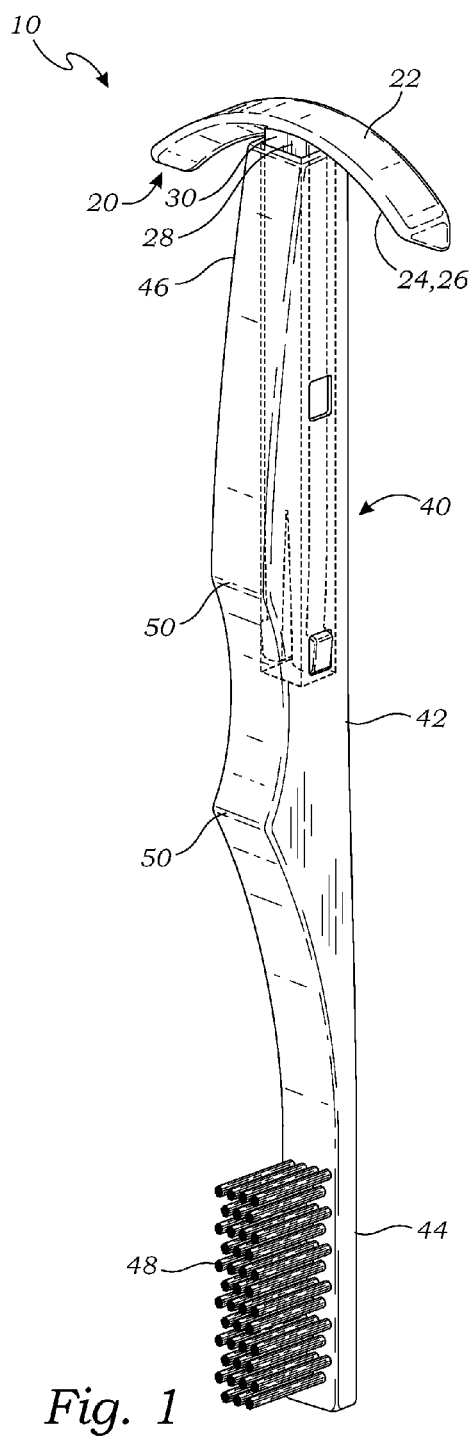
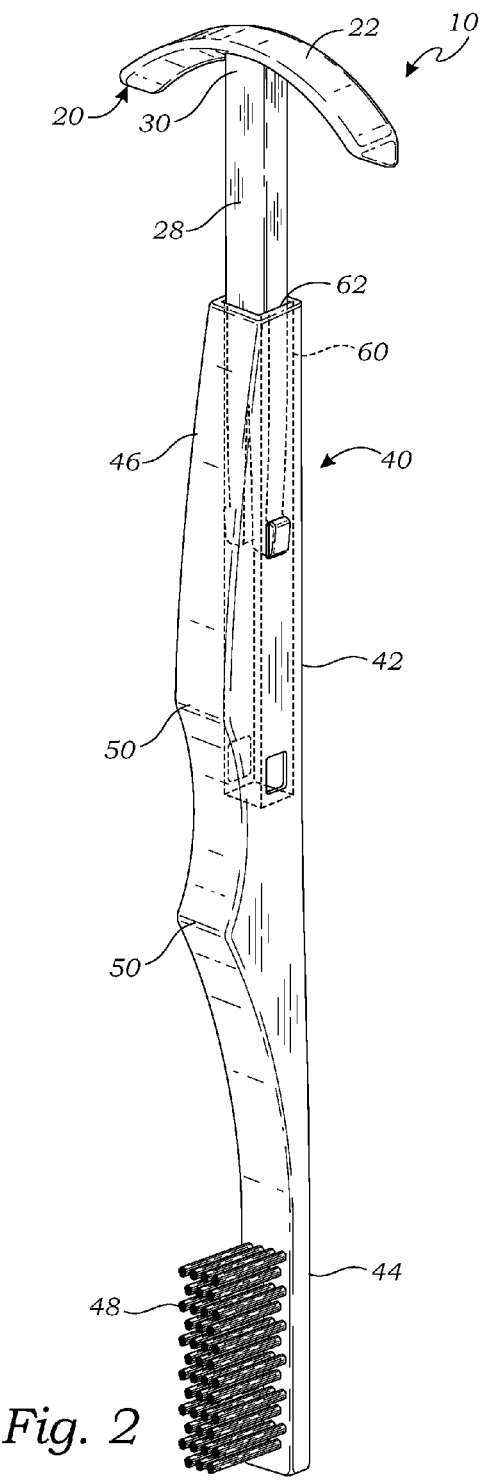
Fig. 1
Fig. 2

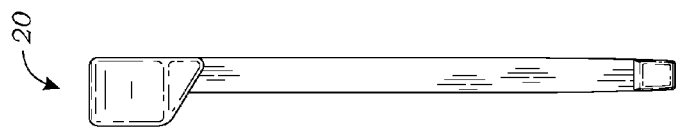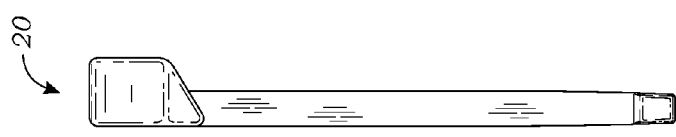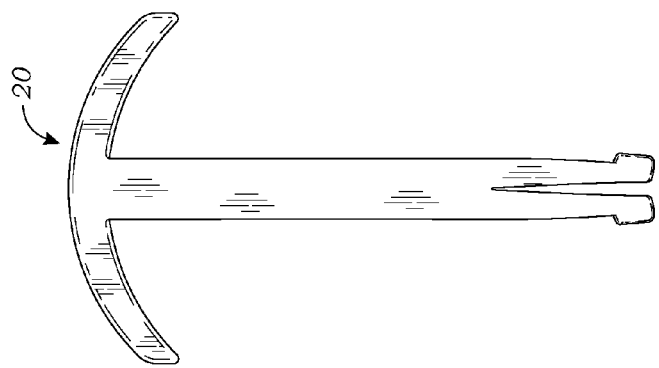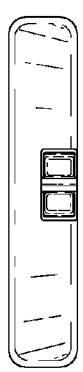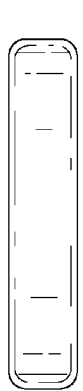

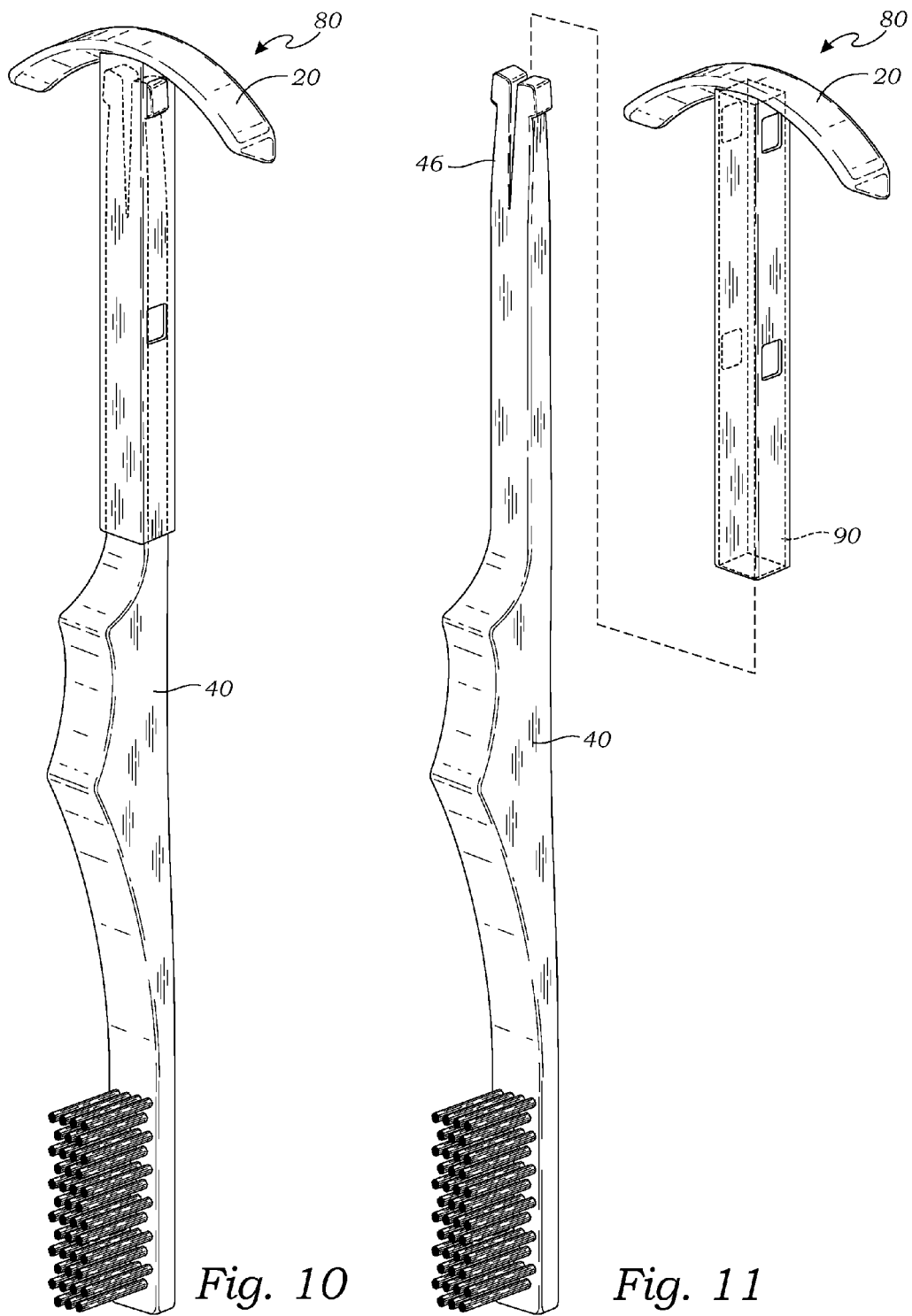

ORAL HYGIENE TOOL

CROSS-REFERENCE TO RELATED APPLICATIONS

This application for a utility patent claims the benefit of U.S. Provisional Application No. 61/923,206, filed Jan. 2, 2014.

BACKGROUND OF THE INVENTION

1. Field of the Invention

This invention relates generally to oral hygiene tools, and more particularly to a tool that includes both a toothbrush and a tongue scraper.

2. Description of Related Art

Tongue scrapers and toothbrushes are common oral hygiene products. The prior art teaches a simple combination of the two tools; however, the resulting device is unwieldy and is either too short to use or too long to store. The present invention addresses those needs by providing a novel and efficient tongue scraper that telescopically engages a toothbrush.

The prior art teaches toothbrushes, tongue scrapers, and the combination of tooth brushes and tongue scrapers. However, the prior art does not teach such a combination with a tongue scraper that telescopically engages a toothbrush, including a locking mechanism for locking the tongue scraper in either a collapsed configuration or an extended configuration. The present invention fulfills these needs and provides further advantages as described in the following summary.

SUMMARY OF THE INVENTION

The present invention teaches certain benefits in construction and use which give rise to the objectives described below.

The present invention provides an oral hygiene tool for scraping a tongue and brushing teeth. The oral hygiene tool has a tongue scraper with an elongate scraper body having an elongate upper edge forming a scraping surface for the tongue, and an elongate connector body having a first end and a second end, the elongate scraper body being connected to the first end transverse to the elongate connector body. The oral hygiene tool also includes a toothbrush with an elongate toothbrush body having a proximal end and a distal end, a plurality of brushes extending from the proximal end of the elongate toothbrush body. The elongate connector body of the tongue scraper is telescopingly engaged with the elongate toothbrush body of the toothbrush, so that the tongue scraper can move between a collapsed configuration and an extended configuration relative to the toothbrush.

A primary objective of the present invention is to provide an oral hygiene tool having advantages not taught by the prior art.

Another objective is to provide an oral hygiene tool with a tongue scraper that telescopically engages a toothbrush.

A further objective is to provide an oral hygiene tool with a locking mechanism for locking the tongue scraper in either a collapsed configuration or an extended configuration.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 1 is a perspective view of an oral hygiene tool in a collapsed configuration, according to one embodiment of the present invention;

FIG. 2 is a perspective view of the oral hygiene tool in an extended configuration;

FIG. 4 is a front elevational view of a tongue scraper of the oral hygiene tool;

FIG. 5 is a rear elevational view thereof;

FIG. 6 is a left elevational view thereof;

FIG. 7 is a right elevational view thereof;

FIG. 8 is a top plan view thereof;

FIG. 9 is a bottom plan view thereof;

FIG. 10 is a perspective view of the oral hygiene tool in the collapsed configuration, according to another embodiment of the present invention, illustrating the tongue scraper having the elongate inner chamber; and FIG. 11 is a perspective view of the oral hygiene tool, illustrating the oral hygiene tool in a disengaged configuration.

DETAILED DESCRIPTION OF THE INVENTION

Figure 3:
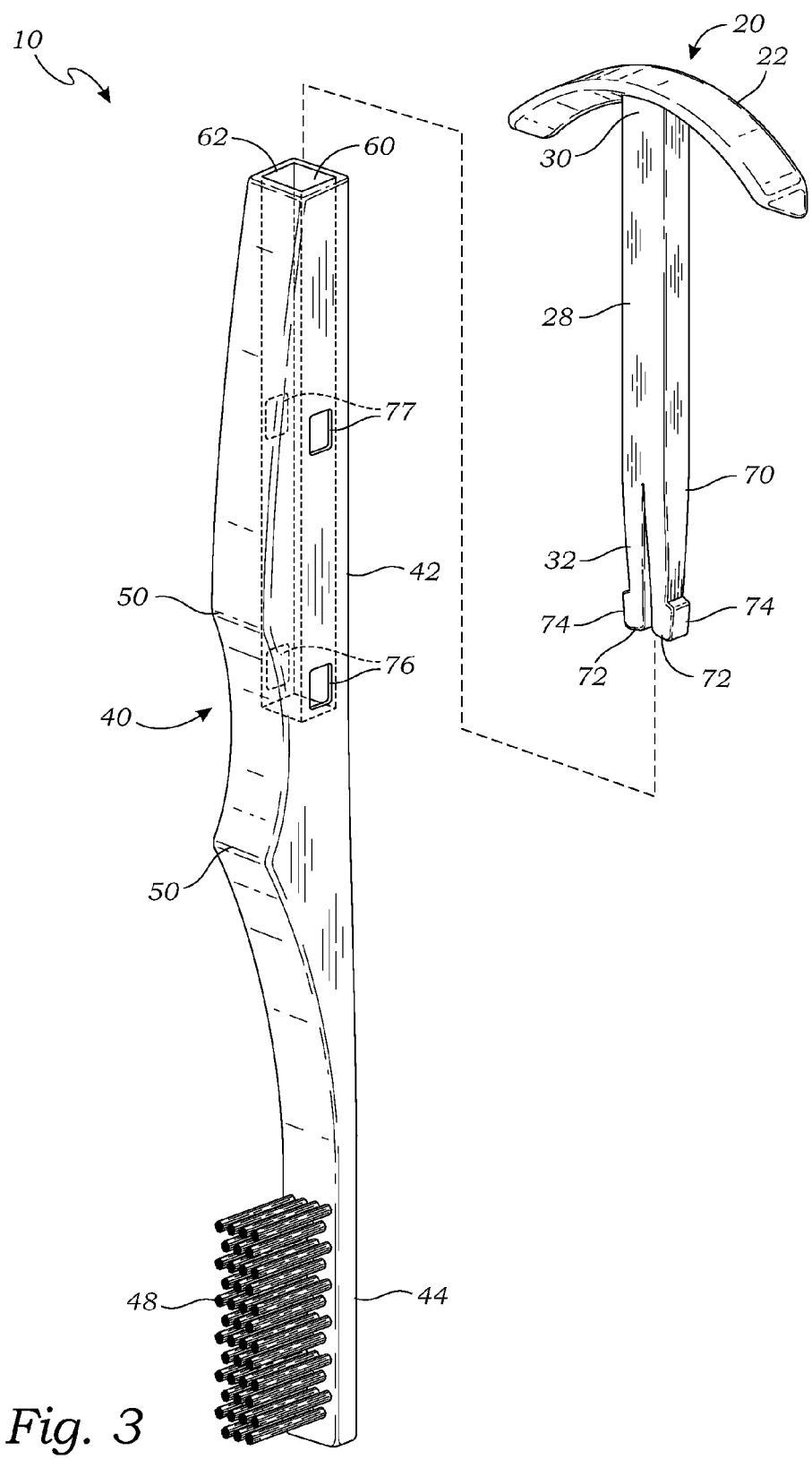
FIG. 3 is a perspective view of the oral hygiene tool in a disengaged configuration.

The above-described drawing figures illustrate the invention, an oral hygiene tool 10 for scraping a tongue and brushing teeth. The oral hygiene tool 10 combines a tongue scraper 20 and a toothbrush 40 that engage each other in an extendable, or telescoping, relationship.

FIG. 1 is a perspective view of the oral hygiene tool 10 in a collapsed configuration, FIG. 2 is a perspective view of the oral hygiene tool 10 in an extended configuration, and FIG. 3 is a perspective view of the oral hygiene tool 10 in a disengaged configuration. As illustrated in FIGS. 1-3, the tongue scraper 20 includes an elongate scraper body 22 and an elongate connector body 28. The elongate scraper body 22 extends laterally on either side of and generally traverse to the elongate connector body 28, and includes an elongate upper edge 24 that is shaped for scraping the tongue. In the present embodiment, the elongate scraper body 22 is curved and has an upwardly extending wedge-shaped cross section that narrows to the elongate upper edge 24. In other embodiments, the elongate scraper body 22 may have an alternative structure with any shape known to one skilled in the art for scraping the tongue, and such alternatives should be considered within the scope of the present invention.

As illustrated in FIGS. 1-3, the elongate connector body 28 of the tongue scraper 20 has a first end 30 and a second end 32. The first end 30 is connected with the elongate scraper body 22. The second end 32 extends outwardly for engaging the toothbrush 40 in a telescoping manner. In the embodiment of FIGS. 1-3, the elongate connector body 28 is a post shaped as an elongate cuboid. In alternate embodiments the elongate connector body 28 may be a structure with any desired shape, e.g. a bar, rod, wedge, or other shape desired by one skilled in the art. In other embodiments, the elongate connector body 28 may have a tapered section (not shown) where the elongate connector body 28 connects to the elongate scraper body 22 so as either not to obstruct, or reduce the obstruction of, the portion of the elongate scraper body 22 that is in contact with the tongue during use. While FIG. 1 illustrates one embodiment of the elongate connector body 28, those skilled in the art may devise alternative embodiments, and these alternative or equivalent are considered within the scope of the present invention.

As illustrated in FIGS. 1-3, the toothbrush 40 has an elongate toothbrush body 42 which may be used as a handle for the toothbrush 40, and which telescopically engages the elongate connector body 28 of the tongue scraper 20. The elongate toothbrush body 42 may have a proximal end 44, a distal end 46, and brushes 48 extending from the proximal end 44 of the elongate toothbrush body 42. The proximal end 44 of the toothbrush 40 is the end of the toothbrush 40 which is inserted into the mouth during use.

As illustrated in FIGS. 1-3, the elongate toothbrush body 42 may also include a plurality of raised sections 50 to aid in the grasping and use of the oral hygiene tool 10, creating an ergonomically suitable handle. The presence of the raised sections 50 may create depressions which conform to functions described above, e.g. providing an ergonomic handle for use, or any other functions desired by one skilled in the art. In alternate embodiments, the raised sections 50 and the depressions may be varied in shape and design to serve any function e.g. providing a gentle or comfortable surface, providing ridges to prevent slippage, providing features such as clasps or releases for storing the oral hygiene tool 10, or any other features desired by one skilled in the art.

The distal end 46 is the end of the elongate toothbrush body 42 which telescopically engages the elongate connector body 28 of the tongue scraper 20. In the embodiment of FIGS. 1-3, the distal end 46 includes an elongate inner chamber 60 shaped to receive the second end 32 of the elongate connector body 28, via a chamber aperture 62. The elongate connector body 28 and the elongate toothbrush body 42 may then telescopically engage each other.

The telescoping construction of the present invention allows several configurations where the length of the oral hygiene tool 10 may be varied according to the needs of the user. In the present embodiment, shown in FIGS. 1-3, the elongate connector body 28 of the tongue scraper 20 may be telescopingly engaged with the elongate toothbrush body 42 of the toothbrush 40, so that the tongue scraper 20 can move between a collapsed configuration and an extended configuration relative to the toothbrush 40. In alternate embodiments, the telescoping of the tongue scraper 20 may be accomplished by a variety of means, e.g. interlocking bodies, tracks, extensions, or any methods desired by one skilled in the art.

As shown in the embodiment of FIGS. 1-3, the elongate inner chamber 60 is within the elongate toothbrush body 42. The inner chamber may have the chamber aperture 62 at the distal end 46 for allowing the elongate connector body 28 to be inserted into the elongate inner chamber 60. The elongate inner chamber 60 may be shaped to allow the elongate connector body 28 of the tongue scraper 20 to telescopically engage the elongate toothbrush body 42.

The elongate inner chamber 60 may have any shape which allows the elongate connector body 28 to telescopically engage with the elongate toothbrush body 42. A square cross-sectional shape, as shown, prevents relative rotation, but in alternative embodiments other cross-sectional shapes may be used. The elongate inner chamber 60 may extend any length longitudinally along the elongate toothbrush body 42. As shown in the embodiment of FIG. 1, one definition of the collapsed configuration may be when the elongate inner chamber 60 is located within the elongate toothbrush body 42 and the elongate connector body 28 is substantially inside the elongate toothbrush body 42. While FIGS. 1-3 illustrate one embodiment of the elongate inner chamber 60, those skilled in the art may devise alternative embodiments, and these alternative or equivalent are considered within the scope of the present invention.

As shown in FIGS. 1-3, the telescoping construction of the oral hygiene tool 10 allows the extended configuration in addition to the collapsed configuration. As shown in FIG. 2, one definition of the extended configuration may be when the elongate inner chamber 60 is located within the elongate toothbrush body 42 and the elongate connector body 28 is substantially, though not completely, outside the elongate toothbrush body 42.

As shown in FIG. 3, the telescopic construction of the oral hygiene tool 10 may allow for the toothbrush 40 and the tongue scraper 20 to be physically separated, which may be defined as the disengaged configuration. In such a configuration, the toothbrush 40 and/or the tongue scraper 20 may be used separately, if desired by a user. In one embodiment, the act of disengagement is reversible, allowing the tongue scraper 20 and the toothbrush 40 to be reassembled. Reassembly may be done by inserting the second end 32 of the tongue scraper 20 through the chamber aperture 62 of the elongate inner chamber 60, thereby re-engaging the tongue scraper 20 and the toothbrush 40. The ability of the oral hygiene tool 10 to be connected together into a single tool which is compact in size enables the oral hygiene tool 10 to be easily transported, stored, and also used while travelling.

As shown in FIG. 3, the oral hygiene tool 10 may further include a locking mechanism 70 for locking the position of the tongue scraper 20 with respect to the toothbrush 40. In the embodiment of FIG. 3, the locking mechanism 70 includes locking apertures 76 and 77, and resilient arms 72 with locking prongs 74 which removably engage the locking apertures 76 and 77 for releasably locking the tongue scraper 20 with respect to the toothbrush 40.

In the present embodiment, there are a first pair of locking apertures 77 located closest to the distal end 46 of the toothbrush 40, and a second pair of locking apertures 76 located between the first pair of locking apertures 77 and the proximal end 44 of the toothbrush 40. The first pair of locking apertures 77 are longitudinally separated and azimuthally aligned with the second pair of locking apertures 76. When the elongate connector body 28 is positioned such that the first pair of locking apertures 77 are engaged, the oral hygiene tool 10 is in the extended position. When the elongate connector body 28 is positioned such that the second pair of locking aperture 76 are engaged, the oral hygiene tool 10 is in the collapsed position. While FIG. 3 illustrates one embodiment of the locking apertures 76 and 77, those skilled in the art may devise alternative embodiments, and these alternative or equivalent are considered within the scope of the present invention.

The resilient arms 72 extend from the elongate connector body 28, and is flexible enough to allow some movement of the resilient arm 72, and in particular, allow a radial deflection which increases towards the second end 32 and which effectively narrows the effective diameter or area of the second end 32. In alternate embodiments, the resilient arm 72 may be constructed differently, e.g. a compressible arm (as opposed to a deflecting arm), or any other sort of resilient arm 72 desired by one skilled in the art. In the present embodiment, there is a pair of the resilient arms 72, each resilient arm 72 being opposite one another azimuthally on the elongate connector body 28. In alternate embodiments, there may be any number of, and orientation of, the resilient arms 72 as desired by one skilled in the art.

The present embodiment may have a locking prong 74 extending radially from the resilient arm 72. In the present embodiment, the locking prong 74 is a protrusion shaped to removably and lockingly engage the locking apertures 76 and 77.

The resilient arm 72 may be pressed away from the locking apertures 76 and 77 to disengage the locking mechanism 70 and allow the elongate connector body 28 to slide longitudinally relative to the connector body 28. In the present embodiment, the locking arm is angled relative to the longitudinal axis such that when a longitudinal force is applied, there is an inward force on the resilient arms 72. If the inward force on the resilient arm 72 is sufficient to deflect the resilient arm 72 inward at the location of the locking prong 74, such that the locking prong 74 disengages from the locking apertures 76 and 77, the locking mechanism 70 will becomes disengaged and allow the telescoping motion of the toothbrush 40 and the tongue scraper 20. In alternate embodiments, other means for engaging/disengaging may be used, e.g. releases, springs, catches, tracks, compression fittings, or any other means desired by one skilled in the art.

FIG. 4 is a front elevational view of the tongue scraper 20, and FIGS. 5-9 are rear, left, and right elevational views, and top and bottom views, of the tongue scraper 20.

FIGS. 10 and 11 are perspective views of a second embodiment of the oral hygiene tool 80. In this embodiment, the male/female relationship between the toothbrush and the tongue scraper may be reversed. In the embodiment of FIGS. 10-11, the elongate connector body 28 of the tongue scraper 20 may include an elongate inner chamber 90 (that is similar to the chamber 60 of FIGS. 1-3), and the distal end 46 of the toothbrush 40 telescopically engages the elongate inner chamber 90.

As used in this application, the term "longitudinally" is taken to be the direction along an axis extending through the elongate connector body and the elongate toothbrush body. The longitudinal direction may then be defined by the direction of the telescoping motion of the elongate connector body and the elongate toothbrush body, described throughout the application. The term "azimuthally" is then the azimuthal or polar coordinate around the axis. The term "radially" is then the radial direction from the axis.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A oral hygiene tool for scraping a tongue and brushing teeth, the oral hygiene tool comprising:
   a tongue scraper comprising:
      an elongate scraper body having an elongate upper edge forming a scraping surface for the tongue; and
      an elongate connector body having a first end and a second end, the elongate scraper body being connected to the first end transverse to the elongate connector body; and
   a toothbrush comprising:
      an elongate toothbrush body having a proximal end and a distal end; and
      a plurality of brushes extending from the proximal end of the elongate toothbrush body;
   the elongate connector body of the tongue scraper being telescopingly engaged with the elongate toothbrush body of the toothbrush, so that the tongue scraper can move between a collapsed configuration and an extended configuration relative to the toothbrush;
   wherein either the elongate connector body or the elongate toothbrush body has an elongate inner chamber shaped to accept, via a chamber aperture, either the elongate connector body or the elongate toothbrush body that does not have the elongate inner chamber;
   wherein the elongate connector body and the elongate toothbrush body slidingly telescopically engage each other;
   further comprising a locking mechanism for removably locking the oral hygiene tool in the collapsed configuration or in the extended configuration;
   at least one resilient arm extending from either the elongate connector body or the elongate toothbrush body;
   a locking prong extending radially from the resilient arm;
   a locking aperture extending radially through either the elongate connector body, or the elongate toothbrush body, to the elongate inner chamber;
   wherein the locking aperture and the locking prong are shaped to removably engage each other, thereby preventing longitudinal motion of the elongate connector body relative to the elongate toothbrush body; and
   wherein the resilient arm may be pressed away from the locking aperture to disengage the locking mechanism and allow the elongate connector body to slide longitudinally relative to the elongate toothbrush body.

2. The oral hygiene tool of claim 1, wherein there are two locking apertures longitudinally spaced and azimuthally aligned on either the elongate connector body or the elongate toothbrush body.

3. The oral hygiene tool of claim 1, further comprising:
   two pairs of the locking apertures, wherein a first pair of locking apertures are longitudinally separated and azimuthally aligned with a second pair of locking apertures and the locking apertures of each pair of locking apertures are azimuthally opposite each other; and
   a pair of resilient arms, each of the resilient arms azimuthally opposite each other and having the locking prong, such that each of the locking prongs may lockingly engage either the first pair of locking apertures or the second pair of locking apertures.

4. The oral hygiene tool of claim 1, wherein the elongate scraper body is curved into a semi-circular shape.

5. The oral hygiene tool of claim 1, the elongate toothbrush body further comprising a plurality of raised sections to aid in the grasping and use of the oral hygiene tool.

6. A oral hygiene tool for scraping a tongue and brushing teeth comprising:
   a tongue scraper comprising:
      an elongate scraper body having an elongate upper edge used as a scraping surface for the tongue; and
      an elongate connector body having a first end and a second end, the first end connected transversely to the elongate scraper body;
   a toothbrush comprising:
      an elongate toothbrush body having a proximal end and a distal end;
      an elongate inner chamber within the elongate toothbrush body having a chamber aperture at the distal end, wherein the elongate inner chamber is shaped to allow the elongate connector body of the tongue scraper to telescopically engage the elongate toothbrush body; and
      a plurality of brushes extending from the proximal end of the elongate toothbrush body; and
   further comprising a locking mechanism for removably locking the oral hygiene tool in a collapsed configuration or in an extended configuration, the locking mechanism comprising:
   at least one resilient arm extending from the elongate connector body;

a locking prong extending radially from the resilient arm;
a locking aperture extending radially through the elongate toothbrush body to the elongate inner chamber;
wherein the locking aperture and the locking prong are shaped to removably engage each other, thereby preventing longitudinal motion of the elongate connector body relative to the elongate toothbrush body; and
wherein the resilient arm may be pressed away from the locking aperture to disengage the locking mechanism and allow the elongate connector body to slide longitudinally relative to the elongate toothbrush body.

\* \* \* \* \*